US00PP22313P2

(12) United States Plant Patent
Egger

(10) Patent No.: US PP22,313 P2
(45) Date of Patent: Dec. 6, 2011

(54) ***HEUCHERELLA* PLANT NAMED 'YELLOWSTONE FALLS'**

(50) Latin Name: ***Heucherella* hybrid**
Varietal Denomination: Yellowstone Falls

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/806,079

(22) Filed: Aug. 4, 2010

(51) Int. Cl.
*A01H 5/00* (2006.01)

(52) U.S. Cl. ..... Plt./441

(58) Field of Classification Search ..... Plt./441
See application file for complete search history.

*Primary Examiner* — Susan McCormick Ewoldt
(74) *Attorney, Agent, or Firm* — Klarquist Sparkman, LLP

(57) ABSTRACT

A new and distinct *Heucherella* plant substantially as shown and described, characterized by its trailing habit combined with yellow spring leaves to lime green summer and winter leaves, a dark splatter pattern on the veins, medium palmately lobed leaves, and good vigor.

1 Drawing Sheet

Botanical denomination: *Heucherella* hybrid.
Variety designation: 'Yellowstone Falls'.
Cross reference to sibling: *Heucherella* 'Redstone Falls' (applied for concurrently, U.S. Plant patent application Ser. No. 12/806,089)

The present invention relates to a new and distinct cultivar of *Heucherella* and given the cultivar name of 'Yellowstone Falls'. *Heucherella* is in the family *Saxifragaceae*. *Heucherella* 'Yellowstone Falls' originated from a controlled cross between *Heuchera* 909-2 (a proprietary unreleased *Heuchera villosa* hybrid), as the seed parent, and massed selected proprietary *Tiarella* trailing, as the pollen parent.

Compared to the seed parent *Heuchera* 909-2, the new cultivar is trailing with creamy white colored flowers rather than clumping with pink flowers.

Compared to the trailing *Tiarella* parent, the new cultivar has yellow to lime leaves rather than green.

Compared to its sibling, *Heucherella* 'Redstone Falls' (U.S. Plant patent application Ser. No. 12/806,089), the new cultivar has yellow to lime foliage rather than purple red to brown to olive green.

This new *Heucherella* is unique in being the first trailing *Heucherella* with yellow to lime leaves. It is further characterized by:

1. yellow spring leaves to lime green summer and winter leaves,
2. a dark splatter pattern on the veins,
3. medium palmately lobed leaves, and
4. good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 6-month-old greenhouse grown *Heucherella* 'Yellowstone Falls' in a 4 inch pot in spring in Canby, Oreg.

FIG. 2 shows a 9-month-old plant in summer in a container in the garden in Canby, Oreg.

DETAILED PLANT DESCRIPTION

The following is a detailed description of the new *Heucherella* cultivar based on observations of a one-year-old specimens growing in a one gallon container in the greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form.*—Basal rosette and trailing, herbaceous perennial.
*Hardiness.*—USDA Zone 4 to 9.
*Size.*—14 cm tall from top of the foliage to the ground and 80 cm wide.
*Habit.*—Mounding and trailing.
*Vigor.*—Excellent.
*Roots.*—Fibrous, freely branching, fine, and white in color.

Stem:

*Size.*—4 mm wide and grows to 33 cm long.
*Internode length.*—2.5 cm usually.
*Stem color.*—Greyed Red 178A in sun and Yellow Green 148C in shade.

Leaf:

*Type.*—Simple.
*Arrangement.*—Rosette and alternate.
*Shape.*—Broadly ovate.
*Lobing/division.*—5 palmate lobes with the terminal the longest, each with shallow secondary lobes.
*Venation.*—Palmate.
*Margins.*—Crenate.
*Apex.*—Mucronulate.
*Base.*—Cordate, overlapping.
*Blade size.*—Grows to 10 cm long and 10 cm wide.
*Surface texture.*—Glandular both surfaces.

*Petiole description.*—Grows to 14 cm long and 2 mm wide, glandular hairs, closest to Yellow Green 148C.

*Leaf color.*—Spring topside Yellow Green 145A with dark splatter pattern on the veins, Greyed Purple 187B; summer topside Yellow Green 144B with the pattern Greyed Purple 187A; bottom side Yellow Green 146C with pattern Greyed Purple 187A.

Inflorescence:

*Size.*—3 cm wide and 15 cm long.

*Type.*—Raceme.

*Number of flowers per raceme.*—About 65.

*Number of racemes.*—About 20.

*Peduncle.*—Grows to 20 cm tall, 2 mm wide at base, glandular hairs, Yellow Green 146D.

*Pedicel.*—Grows to 4 mm long, with glandular hairs, Yellow Green 146D tinted Greyed Purple 178A.

*Bloom period.*—April to July in Canby, Oreg.

Flower bud:

*Size.*—1.5 mm wide and 3 mm long.

*Description.*—Glandular puberulent, ovoid.

*Color.*—White N155B.

Flower:

*Type.*—Perfect.

*Shape.*—Campanulate.

*Size.*—5 mm deep and 4 mm wide.

*Petal description.*—5 in number, oblanceolate, 4 mm long, tip acuminate, base attenuate, margin entire, glabrous and White NN155B on both sides.

*Calyx description.*—4 mm deep and 4 mm wide, with 5 lobes, divided ½ way to the base, campanulate, glandular hairs on both sides, tip acute, margin entire, White NN155B.

*Stamen description.*—5 in number, filaments 4 mm long, White NN155A, anthers sterile, less than 1 mm, White NN155A.

*Pistil description.*—One central two beaked pistil, 5 mm long, White NN155A.

*Fragrance.*—None.

*Lastingness.*—Each raceme blooms for about 2 weeks on the plant.

Fruit and seed: None

Disease and pest tolerance: No known resistances. Excellent disease tolerance to powdery mildew. All *Heucherella* are susceptible to root weevils.

I claim:

1. A new and distinct *Heucherella* plant as herein illustrated and described.

* * * * *

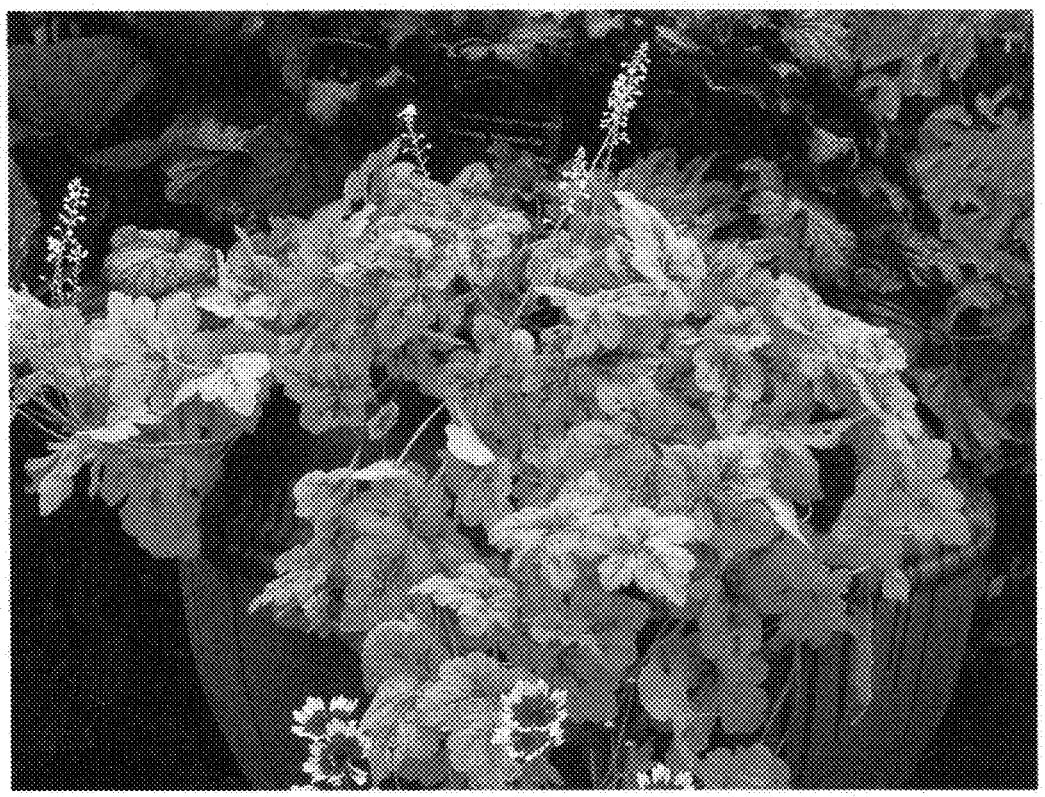

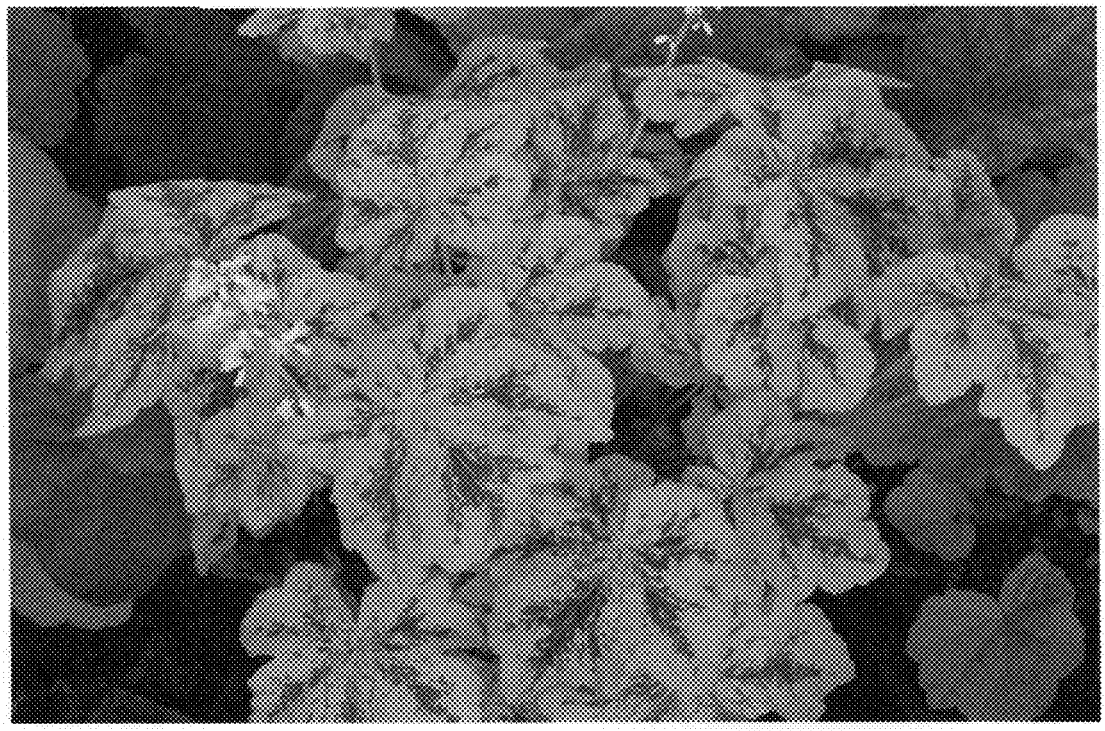
Figure 1 above. Figure 2 below.